US00PP32608P2

(12) United States Plant Patent
van Duijn

(10) Patent No.: US PP32,608 P2
(45) Date of Patent: Dec. 8, 2020

(54) ***ZAMIOCULCAS* PLANT NAMED 'DUYZAM1801'**

(50) Latin Name: ***Zamioculcas zamiifolia* (hort. Lodd.) Engl.**
Varietal Denomination: DUYZAM1801

(71) Applicant: Duynplant B.V., De Lier (NL)

(72) Inventor: Martin van Duijn, De Lier (NL)

(73) Assignee: Duynplant B.V., De Lier (NL)

( * ) Notice: Subject to any disclaimer, the term of this patent is extended or adjusted under 35 U.S.C. 154(b) by 0 days.

(21) Appl. No.: 16/873,495

(22) Filed: Apr. 21, 2020

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

'DUYZAM1801' is a new and distinctive *Zamioculcas* plant which is characterized by a relatively tall plant height, large leaves arising directly from tubers, and leaves comprised of dark green leaflets born on long light brown petioles and an abundance of dark green foliage. The new plant propagates successfully by leaf cuttings and has shown to be uniform and stable in the resulting generations from asexual propagation.

2 Drawing Sheets

Latin name of the genus and species: The Latin name of the genus and species of the novel variety disclosed herein is *Zamioculcas zamiifolia* (hort. Lodd.) Engl.

Variety denomination: The inventive variety of *Zamioculcas* disclosed herein has been given the variety denomination 'DUYZAM1801'.

BACKGROUND OF THE INVENTION

Parentage: 'DUYZAM1801' is a naturally occurring whole-plant mutation of an unnamed *Zamioculcas zamiifolia* plant (not patented) which was discovered by the inventor in May of 2016 at a commercial greenhouse in De Lier, The Netherlands. The mutation was noted for its tall plant height with large dark green leaflets borne on a light brown petiole.

Asexual Reproduction: Asexual reproduction of 'DUYZAM1801' was first accomplished in May of 2016 by way of stem cuttings at a commercial greenhouse in De Lier, The Netherlands. Six successive generations produced from stem cuttings have shown that the unique features of the instant cultivar are stable and reproduce true to type.

SUMMARY OF THE INVENTION

The cultivar 'DUYZAM1801' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Zamioculcas* plant, 'DUYZAM1801'. These traits, in combination, distinguish 'DUYZAM1801' as a new and distinct cultivar.

1. *Zamioculcas* 'DUYZAM1801' exhibits a tall plant height; and

2. *Zamioculcas* 'DUYZAM1801' exhibits large, pinnately compound foliage, which arises directly from tuberous rhizomes; and
3. *Zamioculcas* 'DUYZAM1801' exhibits dark green, glossy obovate to elliptic leaflets borne on long light brown petioles.
4. *Zamioculcas* 'DUYZAM1801' exhibits leaflets that are slightly carinate, revolute, and longitudinally curled downward at and towards the apex.

BOTANICAL DESCRIPTION OF THE PLANT

Figure 1:
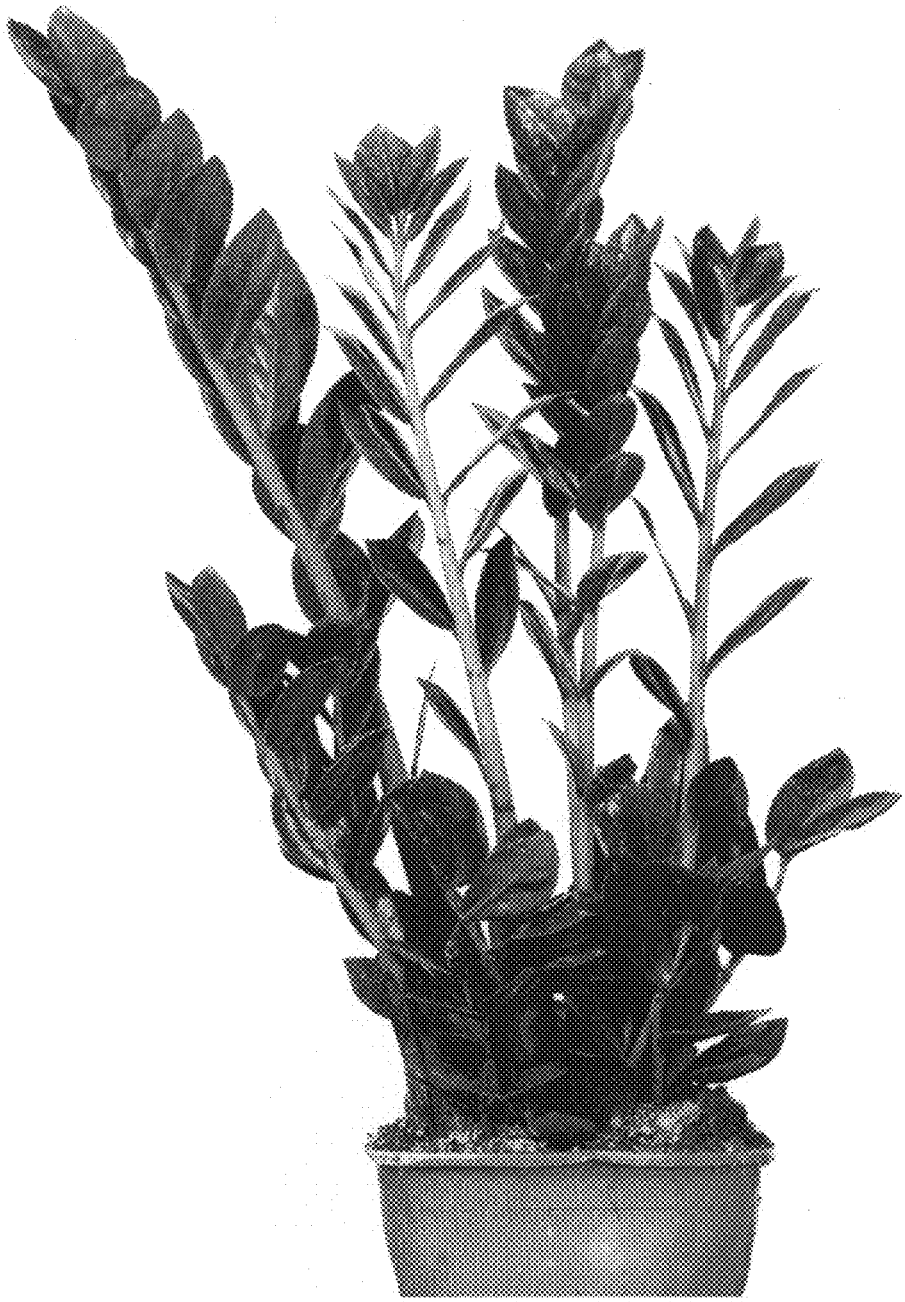
FIG. 1 shows, as nearly true as it is reasonably possible to make the same in color illustrations of this type, the typical foliage and growth characteristics of the new cultivar, 'DUYZAM1801'. The plant shown is approximately 18 months old, potted into a 14 cm nursery pot, grown at a commercial greenhouse in De Lier, The Netherlands.
Figure 2:
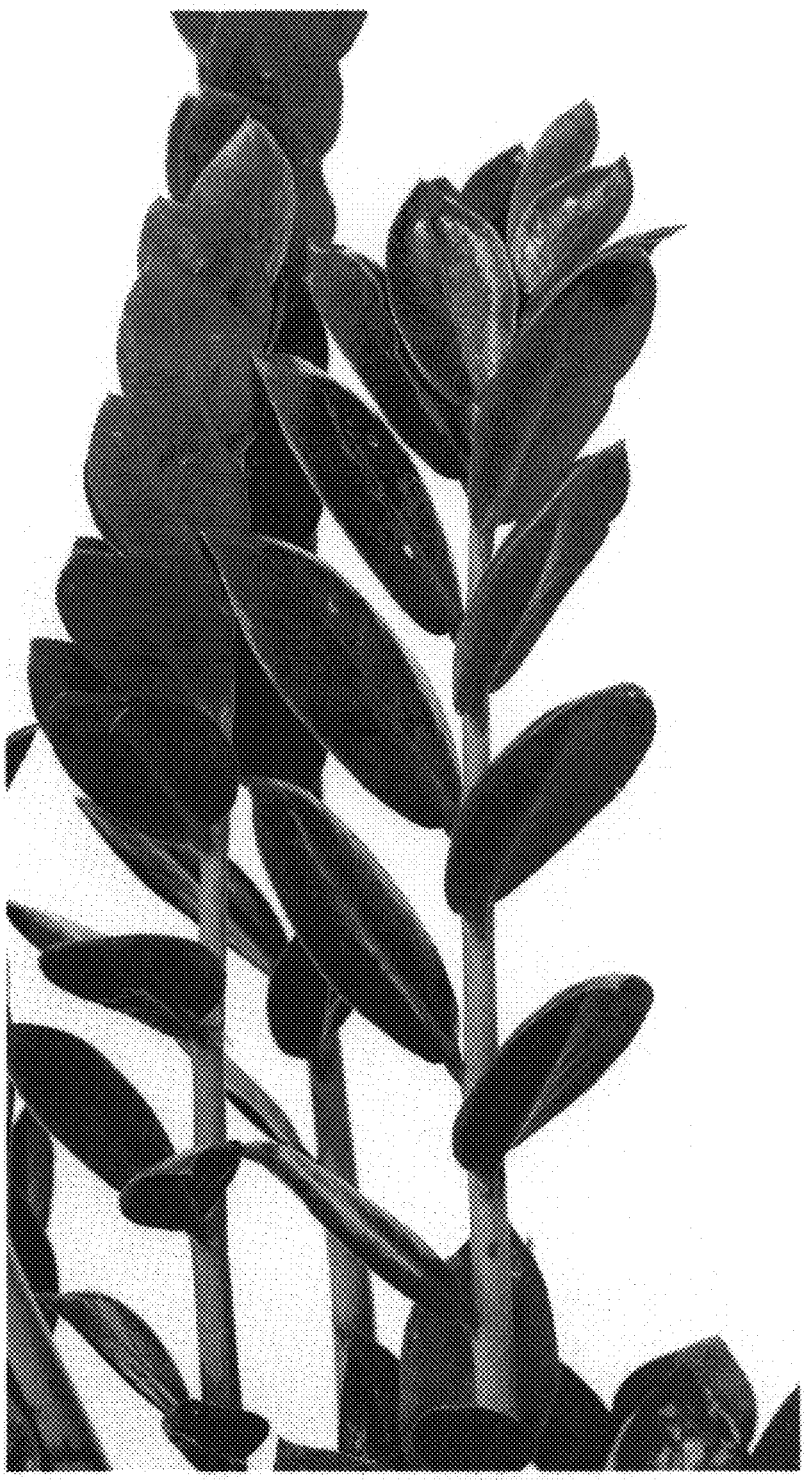
FIG. 2 shows, as nearly true as it is reasonably possible to make the same in color illustrations of this type, the typical foliage of the plant in FIG. 1.

The following is a detailed botanical description of a new and distinct variety of *Zamioculcas* hybrid known as 'DUYZAM1801', based upon observations of 18 month old plants, potted into 14 cm nursery pots and grown indoors at a commercial nursery in De Lier, The Netherlands. Plants were grown in partial shade using accepted fertility and irrigation practices for *Zamioculcas* plants. With the exception of preventative fungicides, no chemical pest control measures were employed. Furthermore, no artificial light or photoperiodic treatments were given to the plants. Observation data was recorded in October of 2019.

Those skilled in the art will appreciate that certain characteristics will vary with older or, conversely, with younger plants. 'DUYZAM1801' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'DUYZAM1801' and comparisons with the parent plant and the most similar variety of common knowledge are provided below.

General plant description:

*Growth habit*.—Tropical evergreen perennial.

*Plant profile shape*.—Narrow inverted triangular to broad oblong.

*Growth rate*.—Moderately fast growing.

*Plant vigor*.—Moderately vigorous to highly vigorous.

*Height*.—42.2 cm to the top of the foliar plane.

*Width*.—25.5 cm.

*Propagation*.—Type — Leaf cuttings. Time to initiate rooting — Approximately 30 days at an approximate temperature of 25 degrees Celsius. Crop time — Approximately 1 year to produce a marketable plant in a 14 cm.

*Pathogen and pest resistance and susceptibility*.—Plants have not been observed to be susceptible or resistant to pathogens and pests common to *Zamioculcas* sp.

*Environmental tolerances*.—Adapt to, at least, USDA Zones 10 to 12 and temperatures ranging from 5 to 40 degrees Celsius; moderate tolerance to rain; low tolerance to wind.

Stem:

*Branching habit*.—No stems or branches; compound leaves in small clumps, arising directly from tuberous rhizomes.

*Number of clumps per plant*.—Four, on average.

*Number of additional clumps formed each year*.—Eight, on average.

Root system:

*Type*.—Tuberous rhizomes bearing thick fleshy roots.

*Shape of rhizomes*.—Irregular oblong to ovoid.

*Dimensions of rhizomes*.—6.2 cm long and 4.1 cm in diameter.

*Density of rhizomes and roots*.—Moderately dense.

*Distribution of rhizomes and roots*.—Rhizomes shallow; roots distributed evenly throughout the soil profile, from shallow to deep.

*Texture of rhizomes and roots*.—Glabrous and very fleshy.

*Color of rhizomes and roots*.—Greyed-green, nearest to a mixture of RHS 195A and 195C.

Foliage:

*Arrangement*.—Compound leaves in small clumps, arising directly from tuberous rhizomes.

*Attachment*.—Petiolate.

*Division*.—Pinnately compound.

*Leaf profile shape*.—Narrow oblong.

*Dimensions*.—31.8 cm long and 7.4 cm wide.

*Attitude*.—Upright; approximately 10 degrees from vertical.

*Quantity*.—Approximately 12 leaves per clump.

*Stipules*.—General — A leafy stipule is present at the base of each pinnately compound leaf. Shape — Ovate. Length — 9.4 cm. Width — 3.3 cm. Apex — Acute. Base — Broad cuneate. Margin — Entire, moderately undulated. Texture — Papery. Color, adaxial and abaxial surfaces — Greyed-orange, nearest to in between RHS 164A and 164B.

*Petiole*.—Aspect — Rounded. Length — 27.9 cm. Diameter — 2.0 cm at the base and 0.6 cm on average. Attitude — Approximately 5 degrees from vertical. Strength — Strong. Texture — Smooth and glabrous. Luster — Matte. Color, adaxial surface — Nearest to in between yellow-green and greyed-green, RHS 148A and 195A, and closest to 195A; irregularly blotched in between yellow-green and greyed-green, RHS 147A and N189A, and closest to RHS 147A. Color, abaxial surface — Nearest to in between yellow-green and greyed-green, RHS 148A and 195A, and closest to 195A; irregularly blotched in between yellow-green and greyed-green, RHS 147A and N189A, and closest to RHS 147A.

*Leaflets*.—Quantity — Typically 16 leaflets. Attitude — Upright. Dimensions — 6.2 cm long and 3.3 cm wide. Shape — Obovate to elliptic. Aspect — Slightly carinate, revolute; longitudinally curled downward, distally. Apex — Abruptly acute. Base — Short attenuate to obtuse. Margin — Entire; not undulated. Texture, adaxial surface — Glabrous and moderately coriaceous. Texture, abaxial surface — Glabrous and moderately coriaceous. Luster, adaxial surface — Very glossy. Luster, abaxial surface — Glossy. Color — Juvenile foliage color, adaxial surface — Nearest to in between green and yellow-green, RHS 139A and 147A. Juvenile foliage color, abaxial surface — Green, nearest to in between RHS NN137B and 143A and closest to NN137B. Mature leaf color, adaxial surface — Nearest to in between green and yellow-green, RHS 139A and 147A, but considerably darker. Mature leaf color, abaxial surface — Green, nearest to in between RHS NN137B and 143A and closest to NN137B. Venation — Pattern — Pinnate. Vein color, adaxial surface — Green, nearest to RHS 137C. Vein color, abaxial surface — Green, nearest to RHS 143C. Petiolule — Length — 0.55 cm. Diameter — Petioles flattened; average width is 0.3 cm and the average height is 0.2 cm. Strength — Strong. Color, adaxial surface — Yellow-green, nearest to RHS 148A. Color, abaxial surface — Darker yellow-green to greyed-green, nearest to RHS 148A and 197A. Texture, adaxial and abaxial surfaces — Glabrous. Luster, adaxial and abaxial surfaces — Slightly glossy.

Inflorescence: No flowering has been observed to date.

COMPARISON WITH THE PARENT PLANT

Plants of the new cultivar 'DUYZAM1801' may be distinguished from its parent, an unnamed *Zamioculcas zamiifolia* plant, by the characteristics described in Table 1.

TABLE 1

| Comparison Between 'DUYZAM1801' and The Parent | | |
|---|---|---|
| Characteristic | 'DUYZAM1801' | The parent |
| Plant height. | Shorter than the parent. | Taller than 'DUYZAM1801'. |
| Leaflet aspect. | Slightly carinate, revolute, and longitudinally curled downward towards the apex. | Flatter than 'DUYZAM1801'. |
| Leaflet size. | Smaller than the parent. | Larger than 'DUYZAM1801'. |
| General coloration of the foliage. | Darker shade of green compared to the parent. | Lighter shade of green compared 'DUYZAM1801'. |

COMPARISONS WITH THE MOST SIMILAR VARIETY OF COMMON KNOWLEDGE

Plants of the new cultivar 'DUYZAM1801' are most similar to the commercial variety, *Zamioculcas* 'EDZAMDARK1' (U.S. Plant Pat. No. 30,529). A comparison of 'DUYZAM1801' with 'EDZAMDARK1' is described in Table 2.

TABLE 2

| Comparison Between 'DUYZAM1801' and 'EDZAMDARK1' | | |
|---|---|---|
| Characteristic | 'DUYZAM1801' | 'EDZAMDARK1' |
| Plant height. | Taller than 'EDZAMDARK1'. | Shorter than 'DUYZAM1801'. |
| Leaflet shape. | Obovate to elliptic. | Elliptic. |
| Leaflet aspect. | Slightly carinate, revolute, and longitudinally curled downward towards the apex. | Slightly carinate, infolded, and longitudinally curled downward towards the apex. |
| General coloration of the foliage. | In between green and yellow green. | Green. |

That which is claimed is:

1. A new and distinct variety of *Zamioculcas* plant named 'DUYZAM1801', substantially as described and illustrated herein.

* * * * *